US009849269B2

(12) United States Patent
Rosenberg et al.

(10) Patent No.: US 9,849,269 B2
(45) Date of Patent: *Dec. 26, 2017

(54) SYSTEM FOR ANCHORING MEDICAL DEVICES

(71) Applicant: INTERRAD Medical, Inc., Plymouth, MN (US)

(72) Inventors: Michael S. Rosenberg, Eagan, MN (US); Mark R. Christianson, Plymouth, MN (US); Andrew T. Forsberg, Plymouth, MN (US); Andrew R. Beeson, Plymouth, MN (US); Ryan J. Bormann, Maple Grove, MN (US); Michael W. Augustine, St. Michael, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 113 days.

This patent is subject to a terminal disclaimer.

(21) Appl. No.: 14/569,065

(22) Filed: Dec. 12, 2014

(65) Prior Publication Data

US 2015/0100025 A1  Apr. 9, 2015

Related U.S. Application Data

(63) Continuation of application No. 13/233,946, filed on Sep. 15, 2011, now Pat. No. 8,936,576.

(51) Int. Cl.
*A61M 25/02*    (2006.01)

(52) U.S. Cl.
CPC ....... *A61M 25/02* (2013.01); *A61M 2025/028* (2013.01); *A61M 2025/0286* (2013.01)

(58) Field of Classification Search
CPC .... A61M 2025/028; A61M 2025/0286; A61M 25/02
(Continued)

(56) References Cited

U.S. PATENT DOCUMENTS 3,039,468 A   6/1962   Price
3,765,032 A   10/1973  Palma
(Continued)

FOREIGN PATENT DOCUMENTS

EP        2002857       12/2008
WO        WO9115254 A1  10/1991
(Continued)

OTHER PUBLICATIONS

European Search Report for Application No. 12832468.8 dated Jun. 2, 2015, 5 pages.
(Continued)

*Primary Examiner* — Kevin C Sirmons
*Assistant Examiner* — Deanna K Hall
(74) *Attorney, Agent, or Firm* — Fish & Richardson P.C.

(57) ABSTRACT

Some embodiments of a medical device anchor system include an anchor device that receives a catheter (or other medical instrument) and secures the catheter in place relative to a skin penetration point. In some embodiments, the anchor device can secure the catheter in an operative position relative to the skin without the use of sutures or skin tapes. In particular embodiments, the anchor device can be adjusted to a folded condition so that subcutaneous anchors are partially rotated prior to removal from the skin penetration point.

20 Claims, 10 Drawing Sheets

(58) Field of Classification Search
USPC .................................................. 604/174, 175
See application file for complete search history.

(56) References Cited

U.S. PATENT DOCUMENTS

| | | | |
|---|---|---|---|
| 3,856,009 A | 12/1974 | Winnie |
| 3,896,527 A | 7/1975 | Miller |
| 3,938,529 A | 2/1976 | Gibbons |
| 4,043,346 A | 8/1977 | Mobley |
| 4,114,618 A | 9/1978 | Vargas |
| 4,164,943 A | 8/1979 | Hill |
| 4,248,224 A | 2/1981 | Jones |
| 4,309,994 A | 1/1982 | Grunwald |
| 4,397,647 A | 8/1983 | Gordon |
| 4,474,569 A | 10/1984 | Newkirk |
| 4,569,344 A | 2/1986 | Palmer |
| 4,592,356 A | 6/1986 | Gutierrez |
| 4,645,492 A | 2/1987 | Weeks |
| 4,665,906 A | 5/1987 | Jervis |
| 4,799,495 A | 1/1989 | Hawkins |
| 4,804,359 A | 2/1989 | Grunwald |
| 4,813,930 A | 3/1989 | Elliott |
| 4,936,823 A | 6/1990 | Colvin |
| 4,986,810 A | 1/1991 | Semrad |
| 5,041,085 A | 8/1991 | Osborne |
| 5,067,957 A | 11/1991 | Jervis |
| 5,122,122 A | 6/1992 | Allgood |
| 5,190,546 A | 3/1993 | Jervis |
| 5,256,146 A | 10/1993 | Ensminger |
| 5,267,960 A | 12/1993 | Hayman |
| 5,279,564 A | 1/1994 | Taylor |
| 5,312,337 A | 5/1994 | Flaherty |
| 5,344,439 A | 9/1994 | Otten |
| 5,368,017 A | 11/1994 | Sorenson |
| 5,378,239 A | 1/1995 | Termin |
| 5,456,671 A | 10/1995 | Bierman |
| 5,496,277 A | 3/1996 | Termin |
| 5,578,013 A | 11/1996 | Bierman |
| 5,597,378 A | 1/1997 | Jervis |
| 5,599,311 A | 2/1997 | Raulerson |
| 5,653,718 A | 8/1997 | Yoon |
| 5,681,288 A | 10/1997 | Schlitt |
| 5,688,247 A | 11/1997 | Haindl |
| 5,702,371 A | 12/1997 | Bierman |
| 5,707,362 A | 1/1998 | Yoon |
| 5,722,959 A | 3/1998 | Bierman |
| 5,728,133 A | 3/1998 | Kontos |
| 5,741,234 A | 4/1998 | Aboul |
| 5,746,720 A | 5/1998 | Stouder |
| 5,755,697 A | 5/1998 | Jones |
| 5,769,821 A | 6/1998 | Abrahamson |
| 5,800,402 A | 9/1998 | Bierman |
| 5,810,781 A | 9/1998 | Bierman |
| 5,814,065 A | 9/1998 | Diaz |
| 5,827,230 A | 10/1998 | Bierman |
| 5,833,664 A | 11/1998 | Seare |
| 5,833,667 A | 11/1998 | Bierman |
| 5,857,999 A | 1/1999 | Quick |
| 5,921,965 A | 7/1999 | Blei |
| 5,928,266 A | 7/1999 | Kontos |
| 5,944,732 A | 8/1999 | Raulerson |
| 5,947,931 A | 9/1999 | Bierman |
| 5,971,960 A | 10/1999 | Flom |
| 5,989,265 A | 11/1999 | Bouquet |
| 6,213,979 B1 | 4/2001 | Bierman |
| 6,290,676 B1 | 9/2001 | Bierman |
| 6,413,240 B1 | 7/2002 | Bierman |
| 6,447,485 B2 | 9/2002 | Bierman |
| 6,540,693 B2 | 4/2003 | Burbank |
| 6,572,588 B1 | 6/2003 | Bierman |
| 6,582,388 B1 | 6/2003 | Coleman |
| 6,582,403 B1 | 6/2003 | Bierman |
| 6,663,600 B2 | 12/2003 | Bierman |
| 6,679,851 B2 | 1/2004 | Burbank |
| 6,695,861 B1 | 2/2004 | Rosenberg |
| 6,770,055 B2 | 8/2004 | Bierman |
| 6,896,665 B2 | 5/2005 | Picha |
| 6,958,044 B2 | 10/2005 | Burbank |
| 7,056,286 B2 | 6/2006 | Ravenscroft |
| 8,235,948 B2 * | 8/2012 | Rosenberg ............. A61M 25/02 |
| | | | 128/DIG. 26 |
| 8,444,603 B2 * | 5/2013 | Rosenberg ............. A61M 25/02 |
| | | | 604/174 |
| 8,579,864 B2 * | 11/2013 | Rosenberg ............. A61M 25/02 |
| | | | 604/174 |
| 8,936,576 B2 * | 1/2015 | Rosenberg ............. A61M 25/02 |
| | | | 604/174 |
| 2002/0068898 A1 | 6/2002 | McGuckin |
| 2002/0068899 A1 | 6/2002 | McGuckin |
| 2002/0120250 A1 | 8/2002 | Altman |
| 2002/0165489 A1 | 11/2002 | McGuckin |
| 2005/0043685 A1 | 2/2005 | Schinkel |
| 2005/0187578 A1 | 8/2005 | Rosenberg |
| 2005/0256458 A1 | 11/2005 | Howard |
| 2006/0058738 A1 | 3/2006 | Ponzi et al. |
| 2007/0078397 A1 | 4/2007 | Weststrate |
| 2007/0225651 A1 | 9/2007 | Rosenberg |
| 2008/0312599 A1 | 12/2008 | Rosenberg |
| 2009/0024090 A2 | 1/2009 | Wright |
| 2009/0099527 A1 | 4/2009 | Rosenberg |
| 2009/0326473 A1 * | 12/2009 | Rosenberg ............. A61M 25/02 |
| | | | 604/180 |
| 2010/0016801 A1 | 1/2010 | Rosenberg |
| 2010/0204656 A1 | 8/2010 | Rosenberg |
| 2012/0016312 A1 * | 1/2012 | Brown .................. A61M 25/02 |
| | | | 604/180 |
| 2012/0078191 A1 | 3/2012 | Rosenberg |

FOREIGN PATENT DOCUMENTS

| | | |
|---|---|---|
| WO | WO 02/11786 | 2/2002 |
| WO | WO2004026152 A1 | 4/2004 |
| WO | WO2005039419 A1 | 5/2005 |
| WO | WO2005102438 A2 | 11/2005 |

OTHER PUBLICATIONS

Johnson & Johnson web page printout, "The EndoANCHOR Comparative Summary" printed Sep. 13, 2005, 2 pages.
Johnson & Johnson web page printout, "The EndoANCHOR Features and Benefits" printed Sep. 13, 2005, 2 pages.
Johnson & Johnson web page printout, "The EndoANCHOR Firing Sequences" printed Sep. 13, 2005, 2 pages.
Web Page Printout of Statlock Device, author and date unknown.
International Search Report and Written Opinion for PCT/US2012/052700, dated Jan. 29, 2013, 10 pages.

* cited by examiner

SYSTEM FOR ANCHORING MEDICAL DEVICES

CROSS-REFERENCE TO RELATED APPLICATION(S)

This is a continuation of U.S. patent application Ser. No. 13/233,946 filed on Sep. 15, 2011, now issued as U.S. Pat. No. 8,936,576, the entire contents of which are incorporated herein by reference.

TECHNICAL FIELD

This document relates to an anchor device, such as a device for use in securing the position of a catheter or another medical instrument.

BACKGROUND

Venous, arterial, and body fluid catheters are commonly used by physicians. For example, such catheters may be used to gain access to the vascular system for dialysis, for introducing pharmaceutical agents, for nutrition or fluids, for hemodynamic monitoring, and for blood draws. Alternatively, catheters can be used for drainage of fluid collections and to treat infection. Following introduction into the patient, the catheter is secured to the patient. In conventional practice, the catheter is commonly secured to the patient using an adhesive tape on the skin or by suturing a catheter hub to the patient's skin.

SUMMARY

Some embodiments of a medical device anchor system include an anchor device that receives a medical instrument (such as a catheter or the like) and secures the instrument in place relative to a skin penetration point. In some circumstances, anchor device may be equipped with a gripping channel that frictionally engages an outer surface of the medical instrument at a location external to skin penetration point. The gripping channel can be shaped in a manner that provides a secure engagement with the medical instrument without necessarily overly compressing the medical instrument. In particular embodiments, the gripping channel can have a cross-sectional shape that is different from the cross sectional shape of the portion of the medical instrument that is engaged therewith. Moreover, the anchor device can be equipped with one or more subcutaneous anchor elements that are configured to abut an underside of a skin layer when deployed in a subcutaneous region. In some embodiments, the portion of each subcutaneous anchor element that is configured to reside under the skin layer can have a generally longitudinally straight shape and a dull or otherwise bulbous tip so as to anchor the remaining external portion of the anchor device in a manner that reduces the likelihood of damage to the tissue surrounding the skin penetration point.

In some embodiments, an anchor device for securing the position of a catheter may include an external retainer assembly to releasably couple to a catheter. The external retainer assembly may have a longitudinal axis extending from a proximal end to a distal end. The anchor device may further include first and second anchors that extend distally from the distal end of the external retainer assembly. Each anchor may comprise a flexible tine that is deployable in a subcutaneous region to secure the external retainer assembly relative to a skin penetration point. The external retainer assembly may define a gripping channel extending generally parallel to the longitudinal axis of the external retainer assembly so as to engage an exterior surface of to the catheter when the external retainer assembly releasably couples to the catheter. The gripping channel may have a non-circular cross-sectional shape in a plane generally perpendicular to the longitudinal axis.

In further embodiments, an anchor device for securing the position of a catheter may include an external retainer assembly to releasably couple to a catheter. The external retainer assembling may have a longitudinal axis extending from a proximal end to a distal end. The anchor device may further include first and second anchors that extend distally from the distal end of the retainer body. Each anchor may comprise a flexible tine that is deployable in a subcutaneous region to secure the external retainer assembly relative to a skin penetration point. Each flexible tine may extend substantially straight to a respective free end having a rounded tine tip. The external retainer assembly may define a channel extending along the longitudinal axis of the external retainer assembly to frictionally engage an exterior surface of to the catheter when the external retainer assembly releasably couples to the catheter.

Some embodiments include a method of using an anchor device. The method may include advancing a catheter though a skin penetration point. The method may include directing an anchor device toward the skin penetration point that is occupied by a portion of the catheter. The anchor device may comprise an external retainer assembly defining a channel to releasably couple to an exterior surface of the catheter arranged outside the skin penetration point, and the anchor device may also comprise first and second anchors extending distally from a distal end of the external retainer assembly. The channel may have a cross-sectional shape that is different than a cross sectional shape of the catheter. The method may further include inserting the first and second anchors through the skin penetration point that is occupied by the catheter so that at least a portion of the first and second anchors are deployed in a subcutaneous region proximate the skin penetration point. The method may also include securing the catheter with the external retainer assembly so that the catheter is anchored relative to the skin penetration point. The method may include pivoting the first and second anchors about a longitudinal fold line defined by a portion of the external retainer assembly so that the first and second anchors are adjusted from a deployed configuration to a removal configuration. Also, the method may include removing the first and second anchors from the subcutaneous region and the skin penetration point.

These and other embodiments may provide one or more of the following advantages. First, some embodiments of an anchor device may be equipped with a gripping channel that frictionally engages an outer surface of the medical instrument at a location external to skin penetration point. The gripping channel can be shaped to releasably retain the medical instrument, such as a catheter, even if the outer surface of the medical instrument has a tapered shape. Moreover, the gripping channel can be shaped in a manner that provides a secure engagement with the medical instrument without necessarily overly compressing the medical instrument. In particular embodiments, the gripping channel can have a cross-sectional shape that is different from the cross sectional shape of the portion of the medical instrument that is engaged therewith.

Second, the anchor device can include one or more subcutaneous anchor elements configured to deploy in a subcutaneous region under the skin proximate to the skin penetration point of the medical instrument. The distal portion of each subcutaneous anchor element that is configured to reside under the skin layer can have a generally longitudinally straight shape and a dull or otherwise bulbous tip so as to anchor the remaining external portion of the anchor device in a manner that reduces the likelihood of damage to the tissue surrounding the skin penetration point. Moreover, the anchor system can be used to releasably retain a medical instrument in a desired position relative to a skin penetration point without necessarily requiring sutures or skin adhesives.

Third, in some embodiments, an anchor device can include a retention portion that readily mates with a medical instrument (such as a catheter) and at least one subcutaneous anchor element extending distally from a distal-most end the retention portion to engage the skin penetration point as the medical instrument. As such, the anchor device may be deployed so that subcutaneous anchor elements are inserted through the skin penetration point that is already occupied by the medical instrument. Such a configuration may allow the anchor device to be used after medical instrument is already in place without the need for a second penetration point for the anchor device.

Fourth, some embodiments of the anchor device can be equipped with structures that promote convenient use for a medical practitioner or other user. For example, the retention member can include a cap alignment feature the reduces the likelihood of improper alignment of a cap member. In addition, the retention member can be equipped with removal tabs that facilitate simplified removal of the cap member even when the user is wearing surgical gloves.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
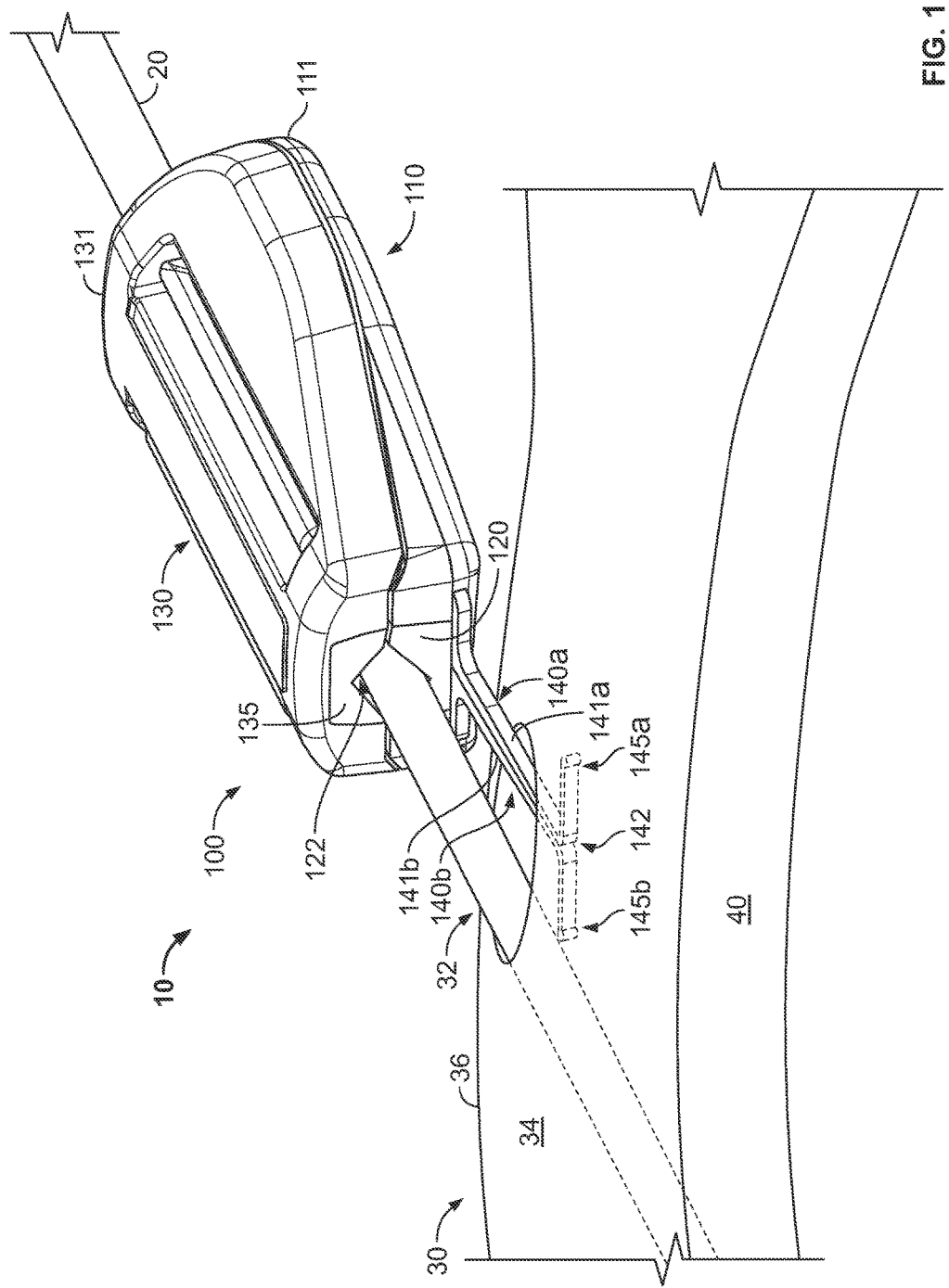
FIG. 1 is a perspective view of an anchor device with a portion of the device located in a subcutaneous region, in accordance with some embodiments.

Referring to FIG. 1, some embodiments of a medical device anchor system 10 include an anchor device 100 that releasably retains a medical instrument 20 (e.g., depicted as a catheter in this embodiment) in an operative position relative to a portion of skin 30 (e.g., relative to a skin penetration point 32). The anchor device 100 may include a base 110 and a cap assembly 130. The base 110 may include a retainer body 111 and one or more anchors 140a-b that extend distally from the retainer body 111 for deployment in a subcutaneous layer 34. The base 110 can receive the medical instrument 20, and the cap assembly 130 can be removably coupled to the base 110 to secure the medical instrument 20 in a generally fixed position relative to the base 110. As described in greater detail below in connection with FIGS. 2-3, the base 110 and the cap assembly 130 can include gripping members 120 and 135, respectively, that at least partially define a gripping channel 122. When the cap assembly 130 is coupled to the base 110, the gripping members 120 and 135 can releasably engage with an outer surface of the medical instrument 20. The gripping channel 122 can be shaped in a manner that provides a secure engagement with the medical instrument 200 without necessarily overly compressing the medical instrument 20. In some embodiments, the cross-sectional shape is non-circular in a plane generally orthogonal to the longitudinal axis of the channel 122. For example, the gripping channel 122 can have a cross-sectional shape (e.g., a generally diamond-shaped cross-section in the depicted embodiment) that is different from the cross-sectional shape of the portion of the medical instrument (e.g., a generally cylindrical cross-sectional shape in this embodiment). In alternative embodiments, the non-circular cross-sectional shape of the channel 122 may be generally polygonal, such as triangular, square, rectangular, pentagonal, hexagonal, or the like, or may be oblong and otherwise different from the cross-sectional shape of the portion of the medical instrument to be engaged. The medical instrument 20 can extend from the gripping members 120 and 135 and through a penetration point 32 in a patient's skin 30 (e.g., through a small incision, a puncture, or the like), while the retainer body 111 and the gripping members 120 and 135 remain outside of the skin 30. In some embodiments, at least a portion of the gripping channel 122 is tapered. For example, the proximal end of the gripping channel 122 is shown to be tapered in FIG. 2, so that the openings on each end of the gripping channel 122 are differently size, as further described below with reference to FIGS. 4A-B.

As described in more detail below, the anchor device 100 can secure the catheter 20 in the operative position relative to the penetration point 32 without necessarily requiring sutures or adhesive tapes bonded to the skin. For example, the base 110 can include the one or more anchors 140a and 140b that extend distally from a distal end of the retainer body 111 so as to penetrate through the same skin opening as the medical instrument 20. The anchors 140a and 140b can include anchor elements 145a and 145b that, after insertion, reside in the subcutaneous region 34 (e.g., a region under the dermal layers of the skin 30 that may comprise a fatty tissue layer) so as to secure the position of the anchor device 100—and the medical instrument 20 retained therein—relative to the penetration point 32. In this embodiment, the anchor elements 145a and 145b are provided as subcutaneous tines that have a generally longitudinally straight shape and a dull or otherwise bulbous tip, a shape that can provide benefits both during manufacture and during use.

Figure 2:
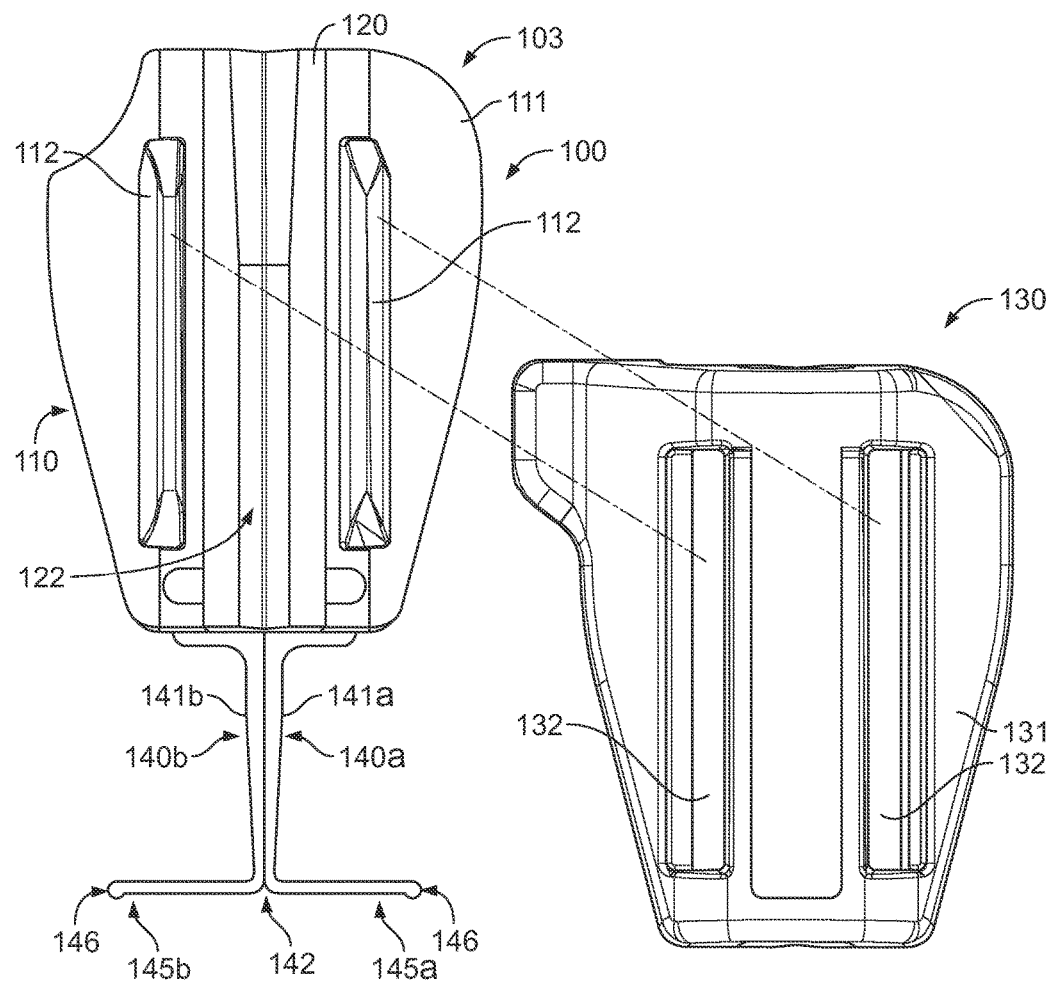
FIG. 2 is a top exploded view of the anchor device of FIG. 1 with the medical device retention portion in an open and deployed configuration.
Figure 3:
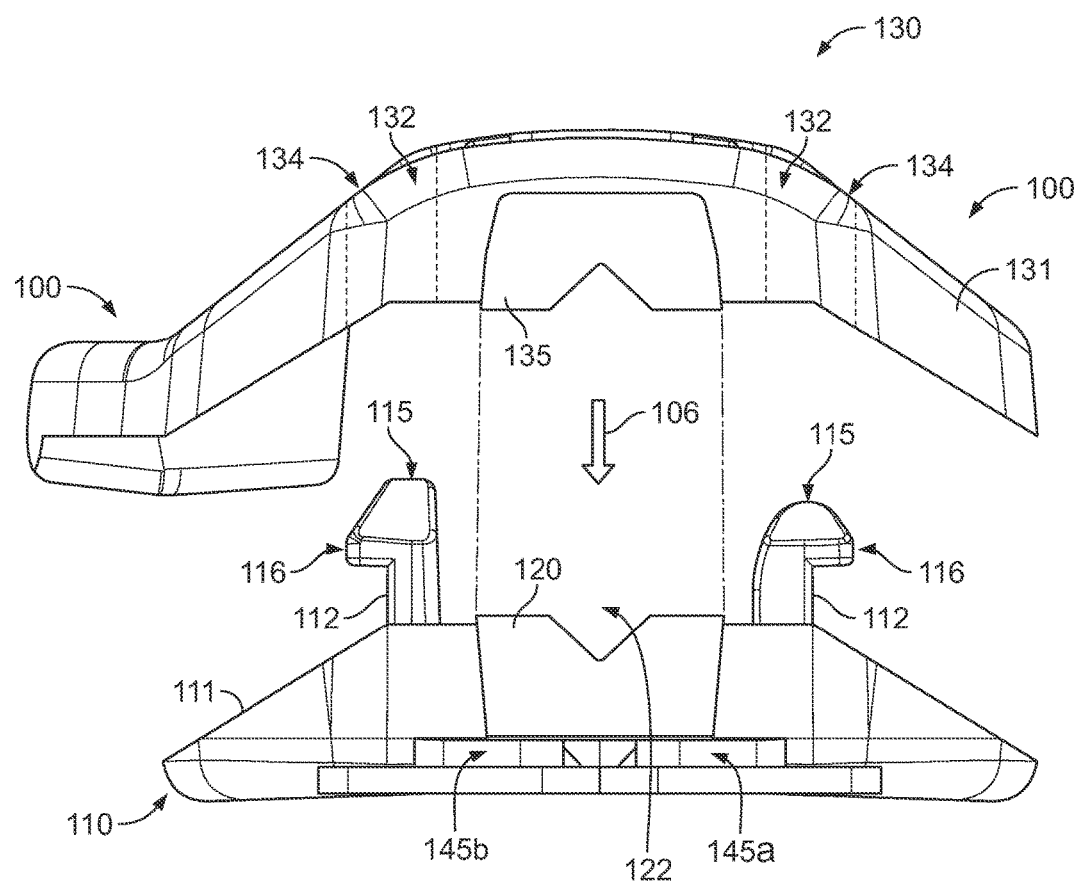
FIG. 3 is a front exploded view of the anchor device of FIG. 1 with the medical device retention portion in an open and deployed configuration

Referring now to FIGS. 1-3, in some embodiments, the medical instrument 20 can include a catheter to be inserted through the penetration point 32 of the skin 30 as part of a medical procedure. For example, in the embodiment depicted in FIG. 1, a central venous catheter 20 can be inserted into a percutaneous opening surgically formed in the skin (e.g., penetration point 32), to the underside of the skin 30, and into a vein 40 to provide vascular access for delivering medications or minimally invasive devices into a patient. After placement of the catheter 20, the base 110 of the anchor device 100 can approach the penetration point 32 such that the tips 142 of the anchors 140a and 140b enter the skin 30 through the penetration point 32. As the anchor device 100 is inserted through the penetration point 32, the tines 145a and 145b are stressed to flex against anchor shafts 141a and 141b (refer also to FIG. 10) so as to pass through the penetration point 32 in a manner that reduces the likelihood of trauma to the surrounding skin tissue. As the anchors 140a and 140b are collectively advanced through the penetration point 32, the tines 145a and 145b are moved beneath the dermal skin layers 36 of the skin 30. When the tines 145a and 145b reach the subcutaneous region 34, the tines 145a and 145b are biased to return toward an unstressed shape, as shown in FIG. 2, thereby deploying in the subcutaneous region 34.

Referring now to FIG. 2, the tines 145a and 145b extend substantially straight to respective free ends having rounded tine tips 146 that reduce the likelihood of the tine tips 146 puncturing the underside of the dermal layers 36. When the tines 145a and 145b of the anchors 140a and 140b are deployed in the subcutaneous region 34, the cap assembly 130 can be removably coupled to the base 110 (refer to FIGS. 4A-4B), compressing the securing portions 120 and 135 of the anchor body 100 causing the securing portions 120 and 135 to releasably engage with an outer surface of the medical instrument 20. In this way, the anchor device 100 can be secured to the patient without the retainer body 111 penetrating though the skin 30 of the patient and without necessarily requiring sutures or adhesive tapes bonded to the skin 30. In one embodiment, tines 145a and 145b are substantially straight and extend generally perpendicular to the shafts 141a and 141b of the anchors 140a and 140b. In other embodiments, tines 145a and 145b create an angle less than 90 degrees in relation to anchors 140a and 140b. This configuration may be preferred as it may reduce the likelihood of the rounded tine tips 146 puncturing the underside of the dermal layers 36. Such a configuration may also be advantageous during the manufacturing process, permitting a high density of tines per square area to be formed on a single sheet of material. Having been manufactured from a sheet of material, the tines have cross-sections that are substantially square-shaped.

Referring now to FIGS. 2-3 and 4A-4B, some embodiments of the anchor device 100 can include structures designed to mate with portions of the medical instrument 20 to be retained by the anchor device 100. The anchor device 100 can include the gripping members 120 and 135 used to secure the catheter 20 (or other medical instrument) relative to the skin penetration point 32. For example, after the catheter 20 is delivered into the targeted vein 40 (or other bodily lumen) and after the tines 145a and 145b are deployed in the subcutaneous region 34, the cap assembly 130 can be removably coupled to the base 110, compressing the gripping members 120 and 135 to temporarily engage with the outer surface of the catheter 20. In this way, the anchor device 100 can be transitioned from the open configuration (shown in FIGS. 2-3) to the closed configuration (shown in FIGS. 4A-4B) to thereby secure the catheter 20 with the gripping members 120 and 135. The gripping members 120 and 135 may comprise a compliant material that provides a frictional engagement with the outer circumferential surface of the catheter 20. For example, the gripping members 120 and 135 may comprise a low durometer thermoplastic elastomer (TPE). As described in more detail below, the retainer body 111 can include locking tabs 112 that can pass through openings 132 in the cap 131 and positively engage at least a portion of perimeters 134 of the openings 132, thereby removably coupling the cap assembly 130 to the base 110.

Still referring to FIGS. 2-3 and 4A-B, the anchor device 100 can include features that facilitate separation from the catheter 20, which can permit the catheter 20 and anchor device 100 to be removed from the skin 30 independently of each other. For example, the tabs 112 may be disengaged from the cap assembly 130 to decouple the cap assembly 130 from the base 110. Once the cap assembly 130 is removed, the gripping members 120 and 135 can release from the catheter 20, thereby allowing the catheter 20 to be moved relative to the anchor device 100. As such, the catheter 20 can be moved independently from the anchor device 100, for example, to withdraw the catheter 20 from the patient while at least a portion of the anchor device 100 remains secured to the skin 30.

Figure 4A:
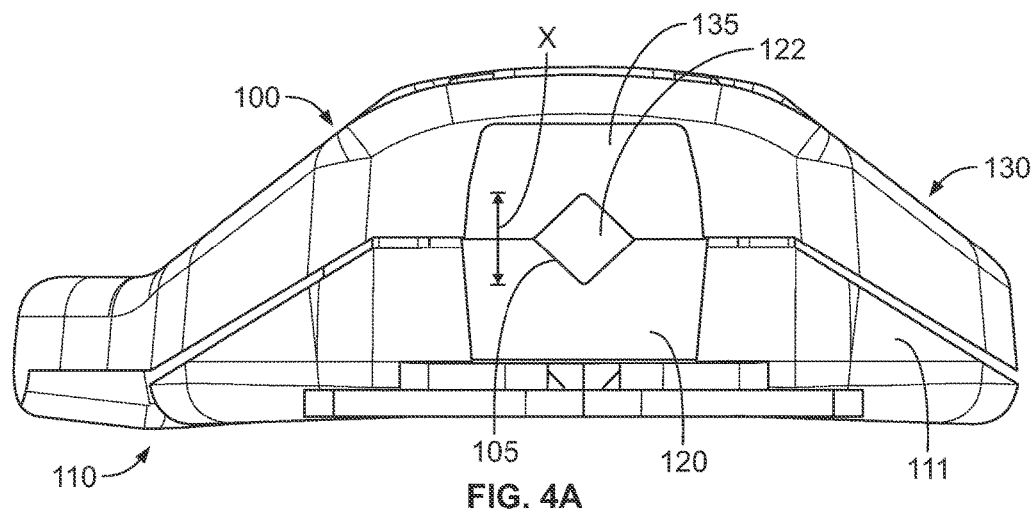
FIGS. 4A-4B are front and rear views, respectively, of the anchor device of FIG. 1 with the medical device retention portion in a closed and deployed configuration.
Figure 4B:
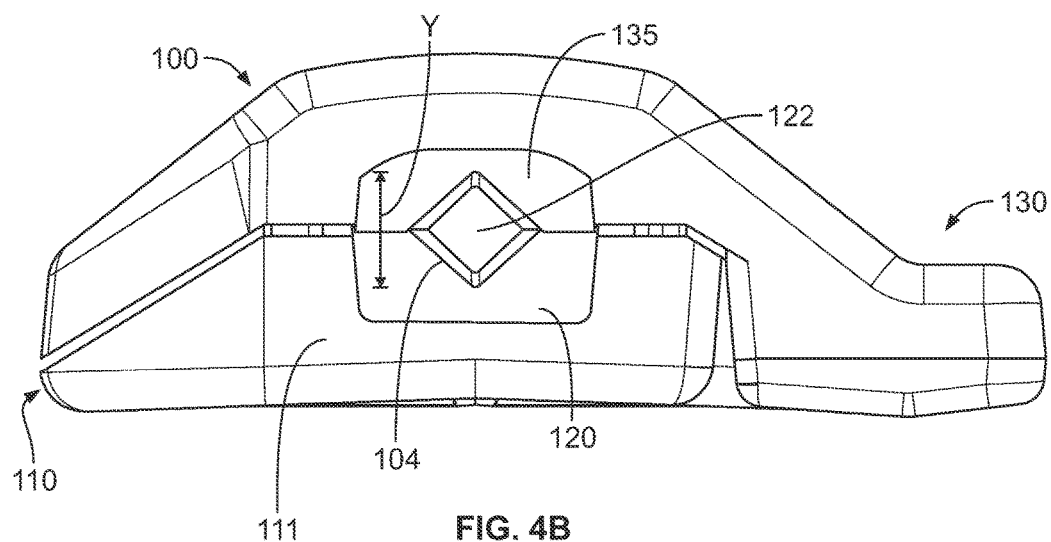

Some embodiments of the anchor device 100 can include structures configured to mate with portions of the medical instrument 20 to be retained by the anchor device 100. For example, when the anchor device is in the closed configuration (as depicted in FIGS. 4A-4B), the gripping members 120 and 135 can define the channel 122 that extends longitudinally from the proximal portion 103 of the anchor device 100 toward the anchors 140a and 140b. The channel 122 can have one or more walls configured to frictionally engage an outer surface of the catheter 20 or other medical instrument to be anchored by the device 100. For example, during installation of the anchor device 100, the anchors 140a and 140b are directed toward the penetration point 32 through which the catheter 20 passes. When the tines 145a and 145b are deployed in the subcutaneous region 34, the cap assembly 130 can be removably coupled to the base 110, which transitions the anchor device 100 to the closed configuration. As shown in FIGS. 4A-4B, openings 104 and 105 can be defined by the base 110 and the cap assembly 130 when arranged in the closed configuration. As such, the catheter 20 can extend though the channel 122 when the anchors 140a and 140b are deployed under the skin 30.

In some embodiments, the channel 122 can have one or more walls that provide a non-circular cross-sectional shape in a plane generally orthogonal to the longitudinal axis of the channel 122. In the particular embodiment shown in FIGS. 4A-4B, the openings 104 and 105 are generally diamond-shaped, and the channel 122 has a generally diamond-shaped cross-section (e.g., including four walls). Such a configuration can conform to releasably engage an outer surface of the catheter 20 in a manner that reduces the likelihood of overly compressing the catheter 20 (which might otherwise hinder operation of the internal catheter lumens). Moreover, the channel 122 having the generally diamond-shaped cross-section can facilitate engagement with a catheter having a tapered outer surface (e.g., a larger outer diameter along a proximal portion than the distal portion). The sizes of openings 104 and 105 are defined by diagonals of lengths X and Y, respectively, as shown in FIGS. 4A-4B, respectively. In some embodiments, length Y is longer than length X, allowing for a better, more secure fit with a catheter 20 having a tapered shaped that decreases in diameter from the proximal portion to the distal portion. As such, in this particular embodiment, the channel 122 has a diamond-shaped cross-section and is tapered so that it is generally wider at a proximal portion of the channel than the distal portion of the channel 122. In other embodiments, length X is longer than length Y, facilitating a catheter that increases in diameter from the proximal end to the distal end.

In some embodiments, the anchor device 100 can be transitioned from the open configuration (FIGS. 2-3) to the closed configuration (FIGS. 4A-4B) when the cap assembly 130 is coupled to the base 110. For example, during installation, the base 110 can be guided so that the anchors 140a and 140b are directed through the penetration point 32 through which the catheter 20 passes. When the tines 145a and 145b are located in the subcutaneous region 34 securing the anchor device 100 relative to the skin 30 (see FIG. 1), the cap assembly 130 can be removably coupled to the base 110 to secure the catheter 20 relative to the anchor device 100, thus securing the catheter 20 relative to the skin 30. In some embodiments, features of the anchor device 100 can removably couple the base 110 to the cap assembly 130. In the example depicted in FIG. 3, the cap assembly 130 can be moved toward the base 110 (e.g., in the direction depicted by arrow 106) to direct the tabs 112 toward to the openings 132. When the diagonal faces of the tabs 112 contact the perimeters 134, the tabs 112 are stressed such that the tips 115 of the tabs 112 move closer to each other. When the face 135 moves beyond the engagement fingers 116, the tabs 112 can outwardly toward their unstressed positions to releasably engage the perimeters 134. When in this closed configuration, the cap assembly 130 and base 110 can apply a compressive force from the gripping members 120 and 135 to the catheter 20 in the channel 122, thereby applying a frictional holding force to the catheter 20 or medical instrument therein.

In some embodiments, the holding force that secures the catheter 20 to the anchor device 100 can be released by separating the cap assembly 130 from the base 110. The cap assembly 130 can be separated from the base 110 by disengaging the locking tabs 112 from the cap assembly 130. For example, the base 110 can be separated from the cap assembly 130 by applying pressure to the locking tabs 112 to move the tips 115 closer to each other. When the engagement portions 116 of the tabs 112 move inside the openings 132 in the cap 131, the retainer portions 120 and 135 force the cap assembly 130 away from the base 110 and the cap assembly 130 becomes decoupled from the base 110, thus transitioning the anchor device 100 to the open configuration (FIGS. 2-3). When the anchor device is in the open configuration, the catheter 20 can be moved relative to the anchor device 100.

Optionally, at least a portion of the anchors 140a and 140b may comprise a material that exhibits superelasticity when used in a patient's body. When the tines 145a and 145b of anchors 140a and 140b are stressed by insertion through the skin penetration point 32, the tines 145a and 145b can superelastically flex from an expanded position (see FIG. 2) to a partially contracted position. In this partially contracted position, at least a portion of the tines 145a and 145b may flex against the anchor shafts 141a and 141b. While against the anchor shafts 141a and 141b, the tines 145a and 145b can readily penetrate through the skin penetration point 32 (which may be generally smaller in width than the width occupied by the tines 145a and 145b in a fully expanded state). Such a feature can reduce the damage to the patient's skin 30 during deployment of the anchors 140a and 140b.

In some embodiments, at least a portion of the anchors 140a and 140b (including the tines 145a and 145b) may be formed from a length of nitinol wire or from a sheet of nitinol material, which has been processed to exhibit superelasticity below or at about a normal human body temperature, such as below or at about 37 degrees C. The nitinol material may comprise, for example, Nickel Titanium (NiTi), Niobium Titanium (NbTi), or the like. Alternatively, the anchors 140a and 140b may comprise a metal material such as stainless steel (e.g., 304 stainless, 316 stainless, custom 465 stainless, and the like), spring steel, titanium, MP35N, and other cobalt alloys, or the like. As previously described, the tines 145a and 145b of the anchors 140a and 140b may extend substantially straight toward the free ends so that an increased number of anchors per square area can be formed on each sheet of the selected metallic material. In another alternative, the anchors 140a and 140b may be formed from a resilient polymer material. In some embodiments, the anchors 140a and 140b can be formed from a material or materials that allow the tines 145a and 145b to be flexed to a contracted position and can resiliently return to an expanded position.

Figure 6:
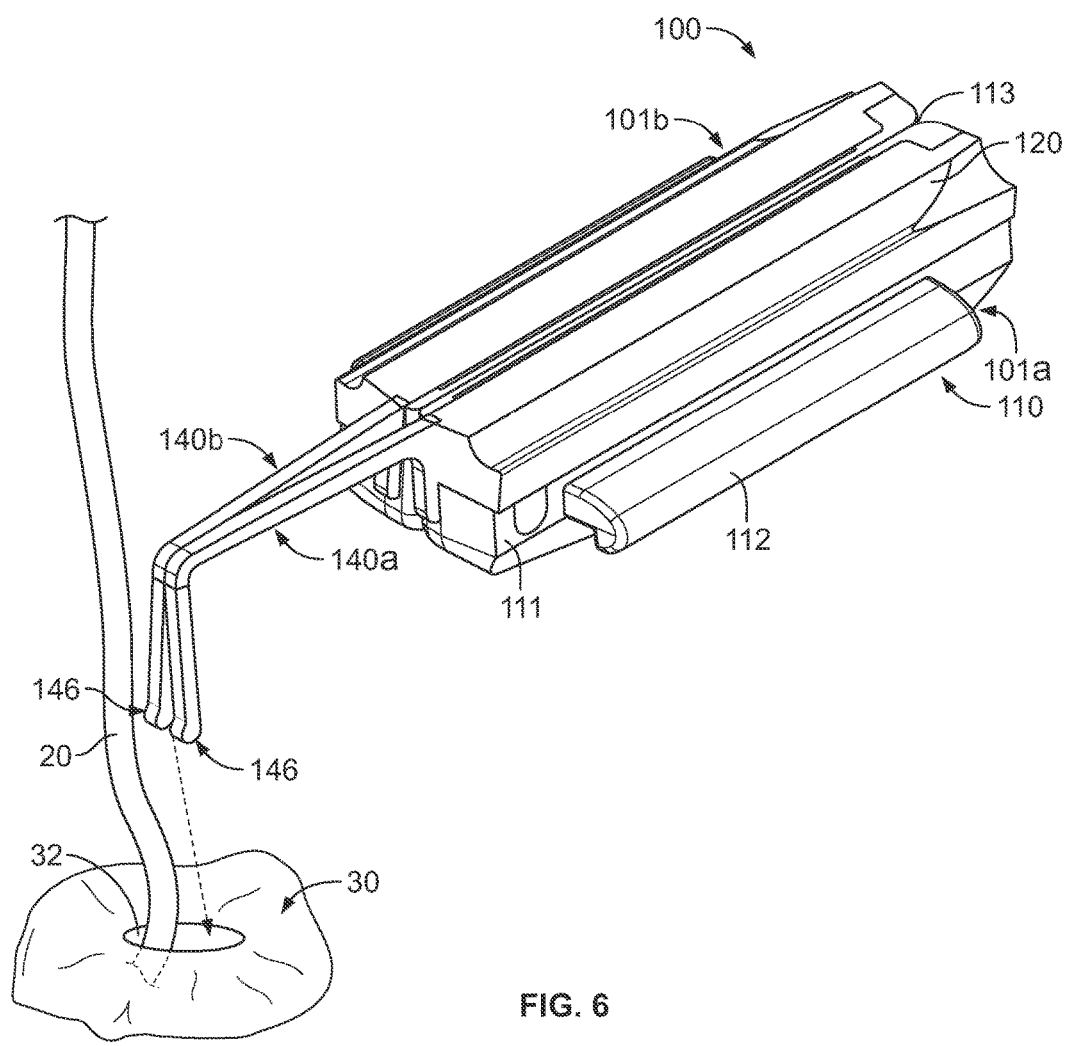
FIG. 6 depicts a perspective view of the anchor device with the anchor device in a folded configuration to facilitate insertion or removal.
Figure 7:
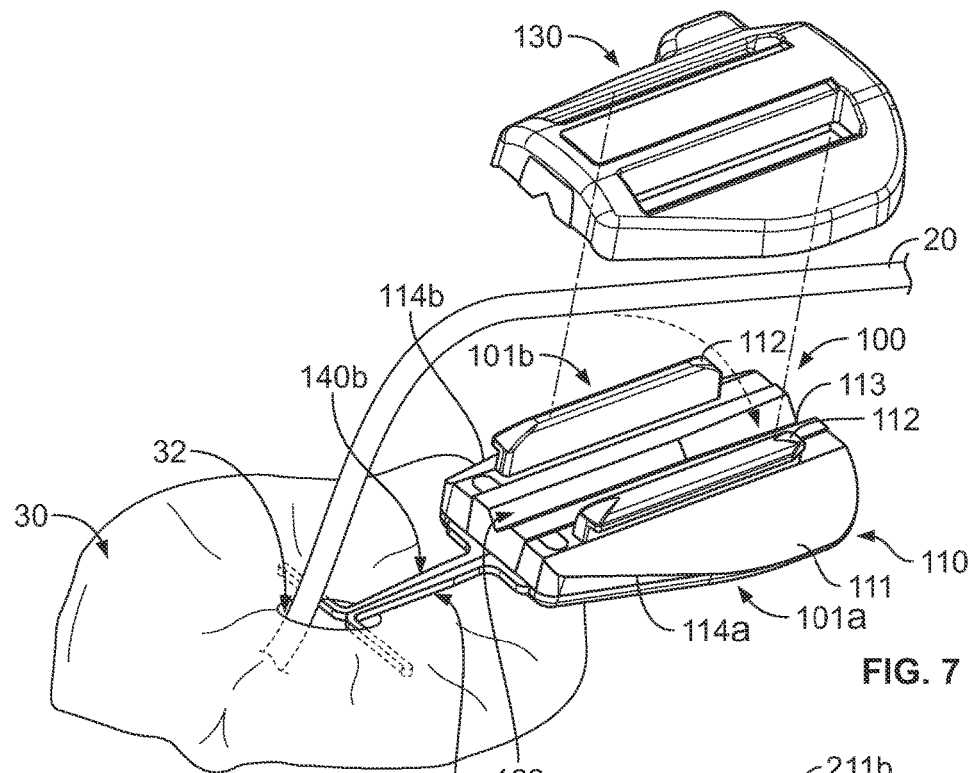
FIG. 7 depicts a perspective view of a method of using an anchor system.

Referring now to FIGS. 6-7, the anchor device 100 can include features that allow the individual anchors 140a and 140b to be moved relative to each other so as to facilitate insertion and removal of the anchor device 100 from the skin 30. In some embodiments, the anchor device 100 comprises a foldable design in which a first portion of the base 110 is pivotably coupled to a second portion of the base 110. For example, the anchor device 100 can include a left portion 101a and a right portion 101b (refer to FIGS. 6-7), which can be flexibly pivoted with respect to each other along a fold line 113 extending longitudinally through the retainer body 111. The left portion 101a can include a left retainer body portion 114a fixedly coupled to the anchor 140a, and the right portion 101b can include a right retainer body portion 114b fixedly coupled to the anchor 140b. Thus, when the left and right retainer body portions 114a and 114b are pivoted about the fold line 113, the two anchors 140a and 140b likewise pivot relative to one another. This process of folding the anchor device 100 can cause the anchor device 100 to transition from a deployed configuration (shown in FIG. 2) where the tines 145a and 145b are oriented to extend in opposing directions to a removal configuration (shown in FIG. 6) where the tines 145a and 145b are generally adjacent to each other and oriented to extend in substantially the same direction. Folding the anchor device 100 into this non-deployed configuration permits the anchors 140a and 140b to be maneuvered in a manner that reduces the likelihood of the tines 145a and 145b causing damage to the skin 30 during insertion and removal. For example, as depicted in FIG. 6, the tines 145a and 145b can be arranged in a generally side-by-side position when the base 110 is in the folded condition, thereby permitting the tines 145a and 145b to be readily inserted (or removed) through the same skin penetration point 32 that is occupied by the catheter 20.

As shown in FIG. 7, methods for using the anchor device 100 may include adjusting the anchor device 100 to the non-folded condition after the subcutaneous tines 145a-b are inserted into the subcutaneous layer 34. As previously described, the free ends of the subcutaneous tines 145a-b extend generally away from one another when the anchor device 100 is shifted to the non-folded condition. In such circumstances, the subcutaneous tines 145a-b are oriented in an anchored position in the subcutaneous layer 34 so as to anchor the retention portion 111 relative to the skin penetration point 32 that is occupied by the catheter 20. When in the anchored position, each of the tines 145a-b can be maintained at generally the same shape as when they were inserted through the skin penetration point (e.g., the generally non-stressed shape in which in which no other components of the anchor system 10 are forcing the tines 145a-b to flex). Accordingly, the tines 145a-b abut against the underside of the skin 30 and the rounded (non-sharp) tine tips 146 help to reduce the likelihood of puncturing the underside of the dermal layers 36 with the dull tips of the tines 146.

After the base 110 of the anchor device 100 is arranged in the non-folded condition with the tines 145a and 145b abutting the underside of the skin 30 near the skin penetration point, the catheter 20 can be shifted into channel of the gripping member 120. As shown in FIG. 7, the catheter 20 can rest on the gripping member 120 of the base 110 while the cap assembly 130 is connected to the base 110. Accordingly, the anchor device 100 releasably engage with the catheter 20 at a location external to the skin penetration point 32 while the anchors 140a and 140b extend distally from the distal end the base 110 to anchor to the skin penetration point 32 (using the subcutaneous anchor tines 145a and 145b). Such a configuration may allow the anchor device 100 to be deployed after the catheter 20 is already in place (through the skin penetration point).

Still referring to FIGS. 6-7, the left and right retainer body portions 114a and 114b can comprise a biocompatible polymer material (e.g., PVC, polypropylene, polystyrene, or the like). In such embodiments, the retainer body 111 can be formed using a molding process in which the retainer body 111 is overmolded around a portion of the anchors 140a and 140b. Next, in a second molding process, an elastomer or other material is molded into the retainer body 111 to create the retainer portion 120 that forms the bottom half of the channel 122. It should be understood from the description herein that the anchor 140b can also be coupled to the retainer body 111 in a similar overmolding process. It should also be understood that there exist other manufacturing processes that can secure the anchors 140a and 140b to the retainer body 111. In some embodiments, the retainer body 111 and the anchors 140a and 140b can be manufactured as a single piece. In some embodiments, the retainer body 111 and retainer portion 120 can be manufactured as a single piece.

Figure 5:
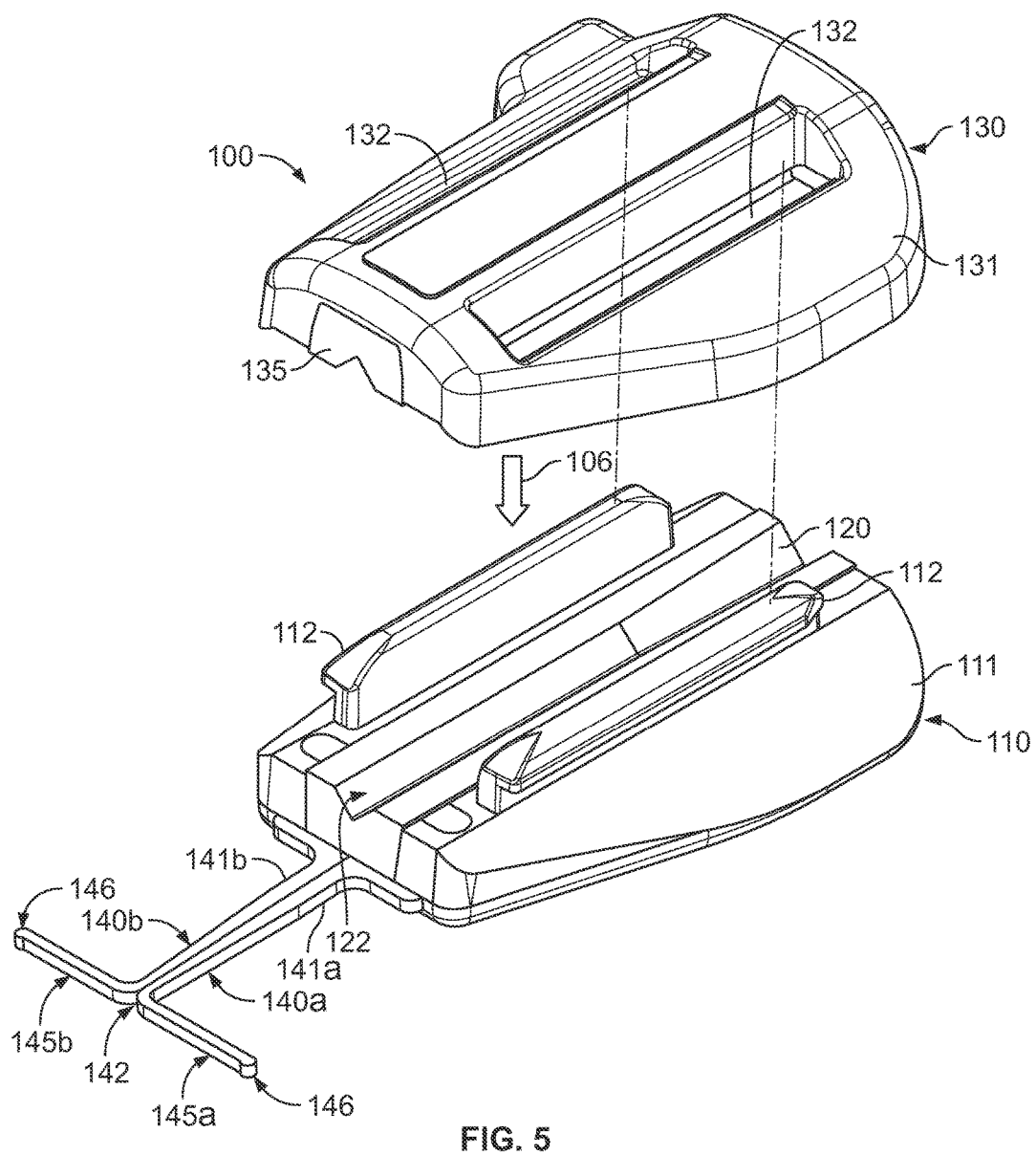
FIG. 5 is an exploded perspective view of the anchor device of FIG. 1.

The left portion 101a of the base 110 and the right portion 101b of the base 110 can be formed as a single component that is bendable along the fold line 113. For example, the retainer body 111 can be configured to resiliently maintain the shape depicted in FIG. 5. The base 110 can be transitioned from the deployed configuration depicted in FIGS. 2-3 to the insertion/removal configuration depicted in FIG. 6 (e.g., when the user desires to insert or remove the anchor device 20 from a patient). At such time, the user may annually apply a bending moment to fold the anchor device 100 along the fold line 113, thus causing the anchor device 100 to transition from the deployed configuration shown in FIGS. 2-3 (where the tines 145a and 145b are substantially oriented in opposing directions) to the insertion/removal configuration shown in FIG. 6 (where the tines 145a and 145b are generally adjacent to each other and oriented in substantially the same direction). In the depicted embodiment, the tines 145a and 145b can be rotated about 75-degrees to about 105-degrees, and preferably about 90-degrees, during the transition to the removal configuration.

Figure 8:
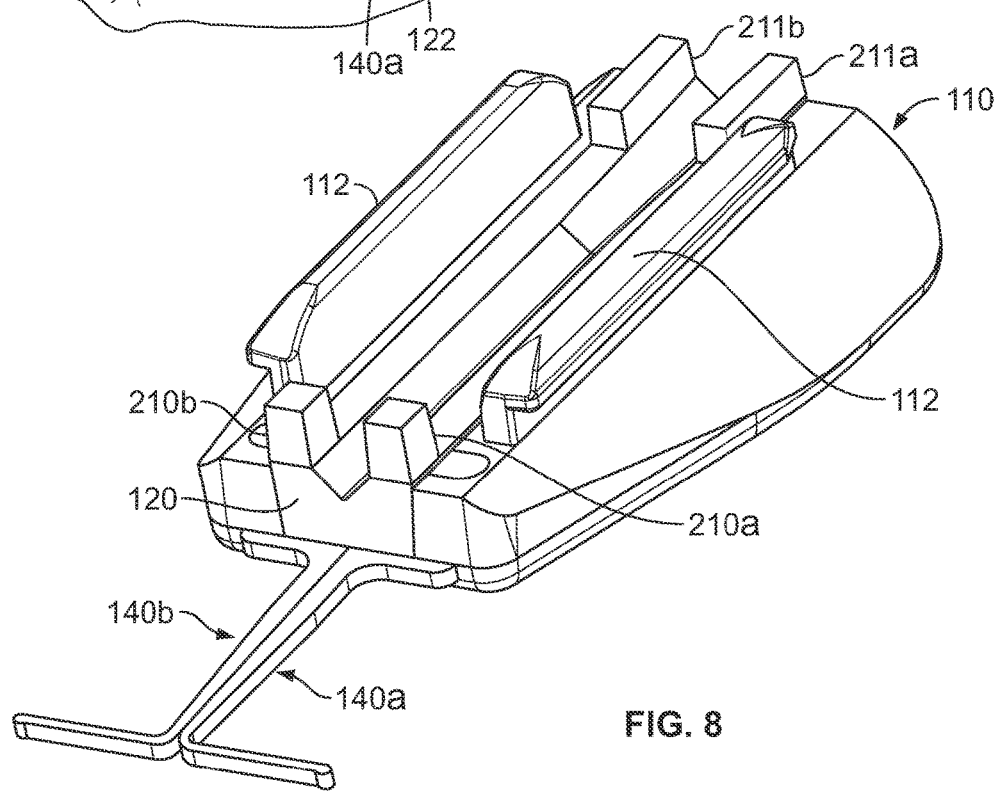
FIG. 8 depicts a perspective view of an anchor device with locating tabs for securing a catheter (not shown).

Referring to FIG. 8, in one embodiment, the base 110 may include one or more locating tabs 210a, 210b, 211a, 211b that serve to align and temporarily retain a catheter 20 prior to engagement with the cap assembly 130. The locating tabs 210a, 210b, 211a, 211b can hold the catheter 20 in a selected axial alignment along the gripping member 120 of the base 110 before cap assembly 130 (FIGS. 4A-B) mates with the base 110 to provide a secure, frictional engagement along the outer surface of the catheter 20. Such an alignment feature provided by the locating tabs 210a-b or 211a-b can be useful, for example, in circumstances where the user is wearing surgical gloves that might reduce the ability to handle the catheter 20 during the attachment of the cap assembly 130 (FIGS. 4A-B). In some embodiments, only front locating tabs 210a, 210b are used, while in other embodiments, only back locating tabs 211a, 211b are used. In a preferred embodiment, both front and back locating tabs 210a, 210b, 211a, 211b are used. During manufacture, locating tabs 210a, 210b, 211a, 211b may be integrally formed as a unitary structure with the gripping member 120 of the base 110. In embodiments that include one or more locating tabs 210a, 210b, 211a, 211b, the gripping member 135 of the cap 130 can define opposing cavities to receive the one or more locating tabs 210a, 210b, 211a, 211b in a complementary manner during attachment of the cap assembly 130 to the base 110.

Figure 9:
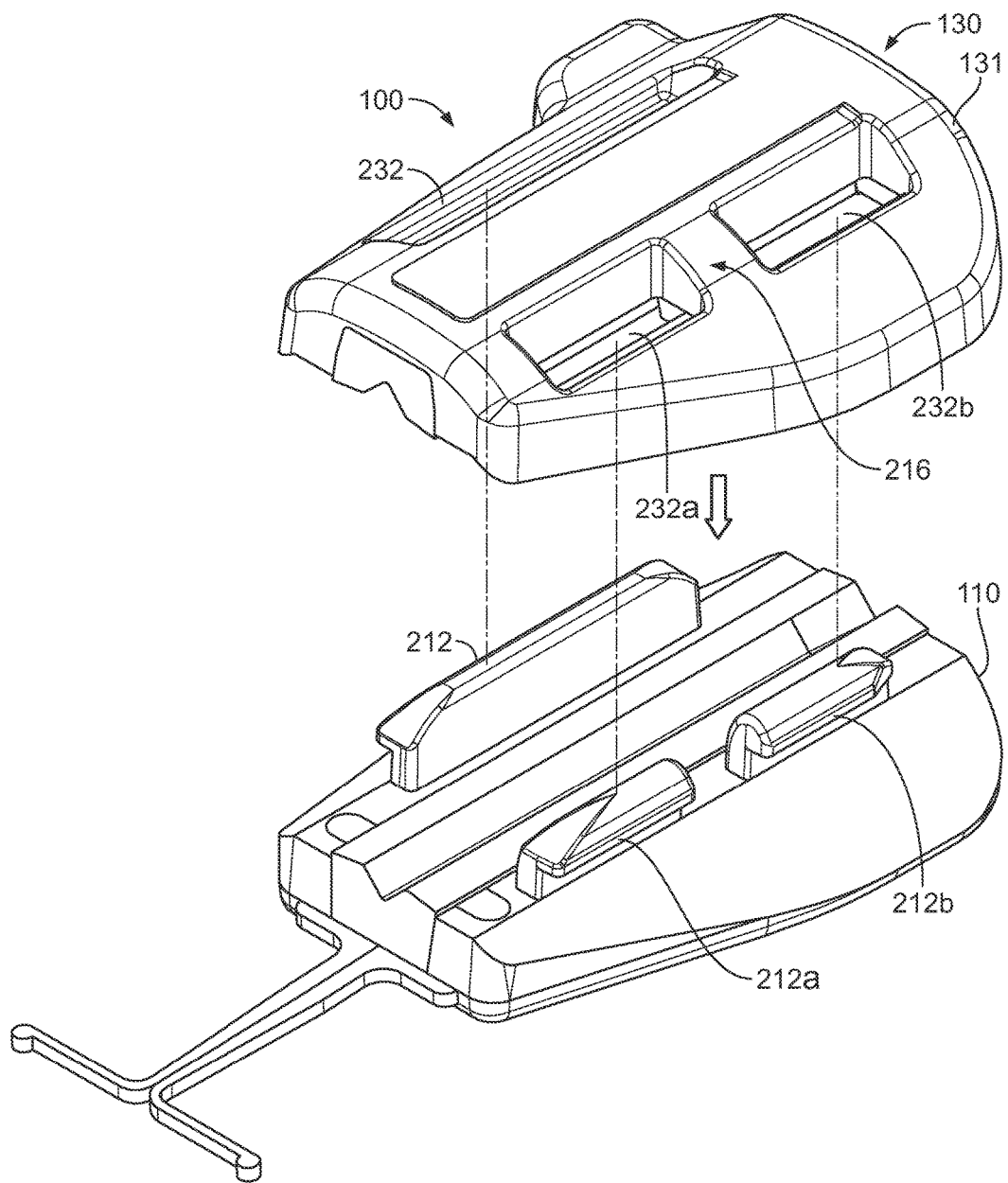
FIG. 9 depicts an exploded perspective view of an anchor device with a cap alignment feature.

Referring now to FIG. 9, some embodiments of the anchor device 100 may include a cap alignment feature that serves to facilitate proper alignment of the cap assembly 130 prior to attachment with the base 110. For example, in order to reduce the likelihood that a user might secure the cap assembly 130 onto the base 110 incorrectly the cap assembly 130 may have non-symmetrical engagement features. In this embodiment, the cap assembly 130 includes a rib 216 on only one side, creating two separate openings 232a and 232b. The opposite side of the cap assembly 130 can have a single opening 232 (rather than two openings separated by a rib). The base comprises three separate tabs 212, 212a, 212b. The larger tab 212 on one side of the base 110 is configured to fit with opening 232, while smaller tabs 212a and 212b on the other side of the base 110 are configured to fit with openings 232a and 232b, respectively. As such, the cap 130 is configured to attach to the base 110 in only one possible orientation when tab 212 is aligned with opening 232 and tabs 212a and 212b are aligned with openings 232a and 232b. Given the location of the rib 216 and the asymmetric design of the cap 130 and base 110, the cap 130 cannot be secured to the base 110 if the tabs 212, 212a, 212b and the openings 232, 232a, 232b are not properly aligned.

Figure 10:
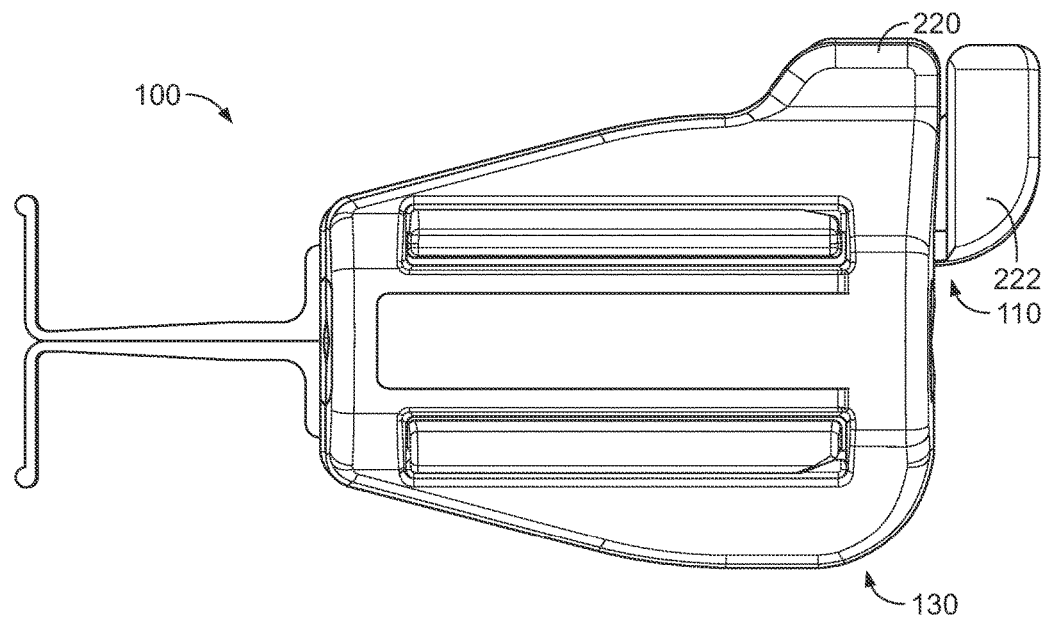
FIG. 10 depicts a top view of an anchor device tabs to assist in removal of the cap of the anchor device.
Figure 11:
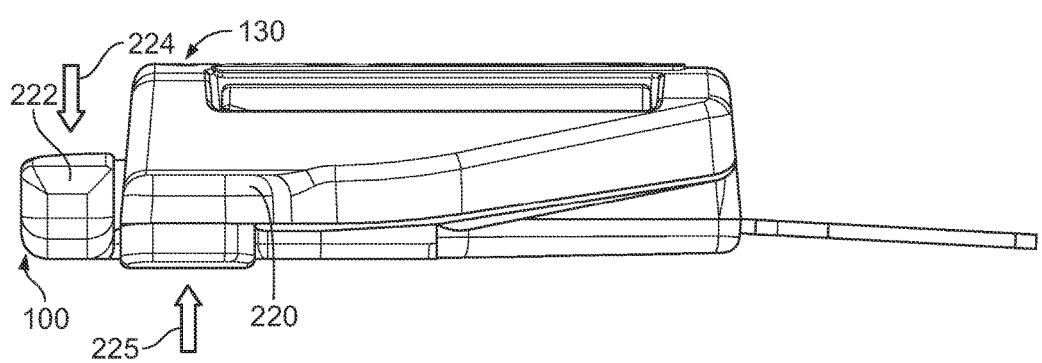
FIG. 11 depicts a side view of the anchor device of FIG. 10.

Referring now to FIGS. 10-11, various embodiments of the anchor device 100 may employ features to assist in the removal of the cap 130 from the base 110. In this particular embodiment, a base tab 222 is used in conjunction with a cap tab 220 to facilitate removal of the cap 130 from the base 110. As shown in FIG. 10, the base tab 222 protrudes slightly away from cap tab 220 so a user can contemporaneously pinch or otherwise grip both the base tab 222 and the cap tab 220 without interference. In this embodiment, at least one of the tabs 220 and 222 extends proximally from a proximal end of the base 110. For example, the base tab 22 may extend proximally rearward of the base 110 so that it is spaced apart from the cap assembly 130. In the example depicted in FIGS. 10-11, the base tab 222 can be gripped by a user and forced (e.g., in the direction depicted by arrow 224) in a direction that is generally opposite from the cap assembly 130 and the cap tab 222. Contemporaneously therewith, the cap tab 220 can be gripped and forced (e.g., in the direction depicted by arrow 225) away from the base 110. In some embodiments, the base 110 may be shaped to provide larger clearance to avoid interference with a user's fingertip when pulling up on the cap tab 220.

Figure 12:
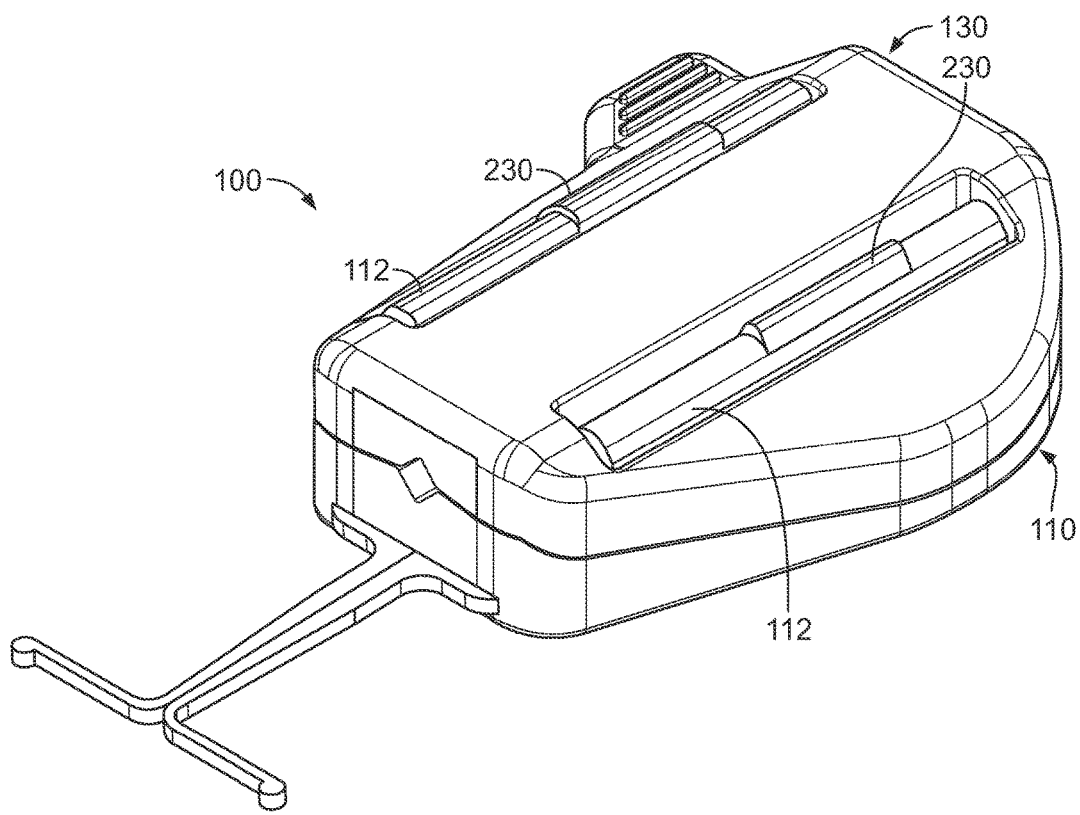
FIG. 12 depicts a perspective view of an anchor device cap removal features.
Figure 13:
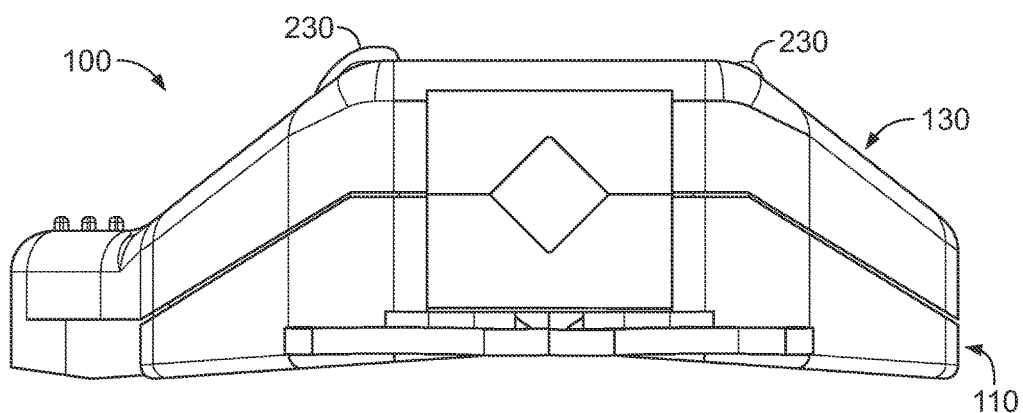
FIG. 13 depicts a front view of the anchor device of FIG. 12.

Referring to FIGS. 12-13, some embodiments of the anchor device 100 may include cap removal features positioned on top of the anchor device 100 so as to simplify removal of the cap assembly 130 from the base 110. For example, the tabs 112 on the base 110 may include cap removal features 230 that extend upwardly above the cap assembly 130. In particular, when the cap 130 is secured to the base 110, the cap removal features 230 protrude above the surface of the cap 130, thereby providing the user with a surface to grip or engage for purposes of manually adjusting the tabs 112. As shown in FIG. 13, the user can manually engage and force the cap removal features 230 at a region above the cap assembly 130 and thereafter force the tabs 112 toward another. Such an action can cause the cap assembly 130 to readily release from the base 110 because the tabs 112 may disengaged from the cavities 112 of the cap assembly 130. Also, in some embodiments, the cap removal features 230 can be used to push the base 110 downward by pushing on the cap removal features 230 while contemporaneously forcing the cap assembly 130 upward.

A number of embodiments of the invention have been described. Nevertheless, it will be understood that various modifications may be made without departing from the spirit and scope of the invention. Accordingly, other embodiments are within the scope of the following claims.

What is claimed is:

1. An anchor device for securing the position of a catheter, comprising:
    means for releasably retaining a portion of a catheter external to a skin penetration point; and
    first and second means for subcutaneously anchoring in a subcutaneous region to secure said catheter retaining means relative to a skin penetration point, wherein the first and second anchoring means are fixedly mounted to said catheter retaining means and extend distally from a distalmost end of said catheter retaining means,
    wherein said catheter retaining means includes a means for gripping an exterior surface of the catheter when said catheter retaining means releasably retains the portion of the catheter, the gripping means extending generally parallel to a longitudinal axis of said catheter retaining means and having a non-circular cross-sectional shape in a plane generally perpendicular to the longitudinal axis;
    wherein at least a portion of said catheter retaining means is foldable between a folded condition and a non-folded condition about a predefined fold axis extending generally parallel to the longitudinal axis, and the first and second anchoring means are fixedly mounted to the foldable portion of said catheter retaining means so that the first and second anchoring means move between the folded condition and the non-folded condition.

2. The anchor device of claim 1, wherein said catheter retaining means comprises a base and a cap that releasably couples with the base so as to define the gripping means therebetween.

3. The anchor device of claim 2, wherein the gripping means comprises a compliant gripper member positioned on each of the base and the cap so as to frictionally engage the catheter with the gripping means when said catheter retaining means releasably retains the portion of the catheter.

4. The anchor device of claim 2, wherein the base further comprises one or more means for aligning the catheter adjacent to the base prior to engagement of the base with a cap.

5. The anchor device of claim 2, wherein the base comprises non-symmetrical engagement features and the cap comprises non-symmetrical engagement features such that the cap is configured to attach to the base in only one orientation.

6. The anchor device of claim 1, wherein the gripping means is at least partially defined by a wall comprising a thermoplastic elastomer material to press against the catheter when said catheter retaining means releasably retains the portion of the catheter.

7. The anchor device of claim 1, wherein the first and second anchoring means extend distally from the distalmost end of said catheter retaining means to deploy into the skin penetration point occupied by the catheter when said catheter retaining means releasably retains the portion of the catheter.

8. The anchor device of claim 1, wherein the non-circular cross-sectional shape of the gripping means comprises a four-sided shape.

9. The anchor device of claim 1, wherein the gripping means comprises a channel having a proximal opening and a distal opening, the proximal opening of the channel being larger than the distal opening of the channel.

10. The anchor device of claim 9, wherein at least a portion of the channel is tapered to provide a larger size at a proximal region of the channel.

11. The anchor device of claim 1, wherein the first and second anchoring means comprise first and second flexible tines, respectively, which extend substantially straight to respective free ends having rounded tine tips.

12. An anchor device for securing the position of a catheter, comprising:
    means for releasably retaining a portion of a catheter external to a skin penetration point; and
    first and second means for subcutaneously anchoring in a subcutaneous region to secure said catheter retaining means relative to a skin penetration point, wherein the first and second anchoring means are fixedly mounted to said catheter retaining means and extend distally from a distalmost end of said catheter retaining means,
    wherein said catheter retaining means includes a means for gripping an exterior surface of the catheter when said catheter retaining means releasably retains the portion of the catheter, the gripping means extending generally parallel to a longitudinal axis of said catheter retaining means and having a non-circular cross-sectional shape in a plane generally perpendicular to the longitudinal axis;
    wherein at least a portion of said catheter retaining means is foldable about a predefined fold axis extending generally parallel to the longitudinal axis, and wherein the first and second anchoring means comprise first and second flexible tines, respectively, which are arranged in a generally side-by-side position when said portion of said catheter retaining means is in a folded condition, and wherein the flexible tines of the first and second anchoring means extend generally away from one another when said portion of said catheter retaining means is in a non-folded condition.

13. The anchor device of claim 12, wherein the first and second anchoring means extend distally from the distalmost end of said catheter retaining means to deploy into the skin penetration point occupied by the catheter when said catheter retaining means releasably retains the portion of the catheter.

14. An anchor device for securing the position of a catheter, comprising:
   means for releasably retaining a portion of a catheter external to a skin penetration point; and
   first and second means for subcutaneously anchoring in a subcutaneous region to secure said catheter retaining means relative to a skin penetration point, wherein the first and second anchoring means are fixedly mounted to said catheter retaining means and extend distally from a distalmost end of said catheter retaining means, wherein a distal portion of each of the first and second anchoring means comprises a flexible tine that is deployable in the subcutaneous region and that extends substantially straight to a respective free end having a rounded tine tip;
   wherein said catheter retaining means includes a means for gripping an exterior surface of the catheter when said catheter retaining means releasably retains the portion of the catheter, the gripping means extending generally parallel to a longitudinal axis of said catheter retaining means; and
   wherein at least a portion of said catheter retaining means is foldable between a folded condition and a non-folded condition about a predefined fold axis extending generally parallel to the longitudinal axis, and the first and second anchoring means are fixedly mounted to the foldable portion of said catheter retaining means so that the first and second anchoring means move between the folded condition and the non-folded condition.

15. The anchor device of claim 14, wherein said catheter retaining means comprises a base and a cap that releasably couples with the base so as to define the gripping means therebetween.

16. The anchor device of claim 15, wherein the gripping means comprises a compliant gripper member positioned on each of the base and the cap so as to frictionally engage the catheter with the gripping means when said catheter retaining means releasably retains the portion of the catheter.

17. The anchor device of claim 15, wherein the base comprises non-symmetrical engagement features and the cap comprises non-symmetrical engagement features such that the cap is configured to attach to the base in only one orientation.

18. The anchor device of claim 14, wherein the flexible tines of the first and second anchoring means are pivoted about 75-degrees to about 105-degrees when the first and second anchoring means are adjusted from a deployed configuration to a removal configuration.

19. The anchor device of claim 14, wherein the first and second anchoring means extend distally from the distalmost end of said catheter retaining means to deploy into the skin penetration point occupied by the catheter when said catheter retaining means releasably retains the portion of the catheter.

20. The anchor device of claim 14, wherein the gripping means comprises a channel having a non-circular, four-sided cross-sectional shape in a plane generally perpendicular to the longitudinal axis.

* * * * *